(12) United States Patent
Sun et al.

(10) Patent No.: US 12,414,853 B1
(45) Date of Patent: Sep. 16, 2025

(54) EXPANDABLE POLYMER HEART VALVE

(71) Applicant: SUZHOU HEARTHILL MEDICAL TECHNOLOGY CO., LTD., Jiangsu (CN)

(72) Inventors: Wei Sun, Suzhou (CN); Xiaoshen Yan, Suzhou (CN)

(73) Assignee: SUZHOU HEARTHILL MEDICAL TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 19/065,513

(22) Filed: Feb. 27, 2025

Related U.S. Application Data (63) Continuation of application No. PCT/CN2024/119305, filed on Sep. 18, 2024.

(30) Foreign Application Priority Data

May 13, 2024 (CN) .......................... 202410586609.5

(51) Int. Cl.
A61F 2/24 (2006.01)

(52) U.S. Cl.
CPC .... *A61F 2/2418* (2013.01); *A61F 2230/0013* (2013.01); *A61F 2230/0069* (2013.01); *A61F 2310/00005* (2013.01)

(58) Field of Classification Search
CPC ......... A61F 2/24; A61F 2/2409; A61F 2/2418
See application file for complete search history.

(56) References Cited

U.S. PATENT DOCUMENTS 4,106,129 A * 8/1978 Carpentier ............ A61F 2/2418
  623/2.18
6,461,382 B1 * 10/2002 Cao ........................ A61F 2/2409
  623/2.19

(Continued)

FOREIGN PATENT DOCUMENTS

CN 116196150 A 6/2023
CN 117257524 A 12/2023

OTHER PUBLICATIONS

Chinese Notification of Grant of Invention Patent issued on Aug. 9, 2024, in corresponding Chinese Patent Application No. 202410586609. 5. (2 pages English, 3 pages Chinese).

(Continued)

*Primary Examiner* — Seema Mathew
(74) *Attorney, Agent, or Firm* — NSIP Law (57) ABSTRACT

Provided by the present invention is an expandable polymeric heart valve. The expandable polymeric heart valve comprises valve leaflets and a valve frame. The valve frame has a hollow cylindrical structure. The valve further comprises an insert adapted to be embedded in the valve frame along an axial direction. The insert is provided with at least one expansion groove in a circumferential direction. The expansion groove has a closed state and an open state. The insert is provided with a limiting structure at an outer wall of the two ends of the expansion groove. The limiting structure defines an expansion width when the expansion groove is in the open state. The present invention achieves expansibility after valve damage while ensuring blood flow properties in the original state of normal use of the valve.

8 Claims, 5 Drawing Sheets

(56) References Cited

U.S. PATENT DOCUMENTS

| | | | | |
|---|---|---|---|---|
| 6,936,067 B2* | 8/2005 | Buchanan | ............. | A61F 2/2409 623/2.14 |
| 7,172,625 B2* | 2/2007 | Shu | ....................... | A61F 2/2409 623/902 |
| 7,455,689 B2* | 11/2008 | Johnson | ................ | A61F 2/2412 623/2.14 |
| 8,034,102 B2* | 10/2011 | Bulman-Fleming | ........................ | A61F 2/2445 623/2.36 |
| 8,062,359 B2* | 11/2011 | Marquez | ............... | A61F 2/2409 623/2.38 |
| 10,543,085 B2* | 1/2020 | Chung | ................. | A61F 2/2445 |
| 11,083,574 B2* | 8/2021 | Sievers | ................ | A61F 2/2418 |
| 11,382,741 B2* | 7/2022 | Eidenschink | ......... | A61F 2/2409 |
| 11,690,714 B2* | 7/2023 | Conklin | ................ | A61F 2/2409 623/1.13 |
| 12,133,796 B2* | 11/2024 | Kaleta | .................... | A61F 2/2412 |
| 2006/0195185 A1* | 8/2006 | Lane | ...................... | A61F 2/2412 623/2.38 |
| 2007/0050021 A1* | 3/2007 | Johnson | ................ | A61F 2/2418 623/2.14 |
| 2007/0260305 A1* | 11/2007 | Drews | ....................... | A61F 2/243 623/2.11 |
| 2011/0276128 A1* | 11/2011 | Cao | ........................ | A61F 2/2409 623/2.11 |
| 2013/0274872 A1* | 10/2013 | Vesely | .................. | A61F 2/2412 623/2.17 |
| 2014/0188221 A1* | 7/2014 | Chung | .................. | A61F 2/2445 623/2.18 |
| 2016/0074161 A1* | 3/2016 | Bennett | ................. | A61F 2/2418 29/890.126 |
| 2017/0000603 A1* | 1/2017 | Conklin | ................ | A61F 2/2409 |
| 2017/0000604 A1* | 1/2017 | Conklin | ................ | A61F 2/2418 |
| 2018/0078366 A1* | 3/2018 | Sievers | ................ | A61F 2/2418 |
| 2018/0289475 A1* | 10/2018 | Chung | .................. | A61F 2/2409 |
| 2019/0046317 A1* | 2/2019 | Murad | .................. | A61F 2/2445 |
| 2019/0240010 A1* | 8/2019 | Hacohen | ............... | A61F 2/2409 |
| 2021/0346154 A1* | 11/2021 | Kaleta | ................... | A61F 2/2418 |
| 2021/0361420 A1* | 11/2021 | Bennett | ................. | A61F 2/2418 |
| 2022/0000612 A1* | 1/2022 | Hacohen | ............... | A61F 2/2418 |
| 2023/0042537 A1* | 2/2023 | Conklin | ................ | A61F 2/2412 |
| 2024/0050227 A1* | 2/2024 | Hacohen | ............... | A61F 2/2418 |

OTHER PUBLICATIONS

International Searching Authority issued Written Opinion on Jan. 8, 2025, in corresponding International Application No. PCT/CN2024/119305. (5 pages in English, 4 pages in Chinese).

* cited by examiner

EXPANDABLE POLYMER HEART VALVE

CROSS-REFERENCE TO RELATED APPLICATIONS

This application claims priority to Chinese Patent Application No. 202410586609.5, entitled "EXPANDABLE POLYMERIC HEART VALVE", filed on May 13, 2024, which is incorporated herein by reference in its entirety.

TECHNICAL FIELD

The present invention relates to the field of medical devices, particularly to an expandable polymeric heart valve.

BACKGROUND ART

In recent years, with the rapid development of interventional treatment technology for valve disease, the clinical application of transcatheter valve technique for the treatment of biological valve damage has become increasingly common. The previously implanted interventional bioprosthetic valve can be damaged for various reasons, and a new valve can be implanted in the damaged valve through the transvascular or transapical approach using catheter technology, avoiding the great trauma and risk caused by secondary thoracotomy for patients. However, in the case of the conventional surgical valve, when the valve-in-valve implantation is performed in the damaged valve, many patients will face the problem of insufficient valve opening area due to the reduction of the valve opening area. Even if a valve-in-valve is implanted via a catheter, it is difficult to achieve good therapeutic effects and its durability will be greatly affected.

Polymer valves, as an emerging type of valve, have many advantages, such as being more durable and not requiring the use of any animal tissue; reducing or eliminating the need for lifelong use of anticoagulant drugs; providing a larger opening area than traditional valves to establish hemodynamics and blood flow similar to human heart valves; adopting mechanized production and manufacturing to achieve better accuracy and quality control, while eliminating the uncontrollability of manual production; having more competitive economic value, etc.

Polymeric valves also face the same problems, namely, the need to implant a new intervention valve after valve damage. The existing artificial heart valves use the overlapping of support structure parts to realize the limit expandable function of the valve. Such design may cause unevenness on the inner wall of the valve, resulting in protrusion on the inner wall of the valve and affecting the blood flow performance in normal use before damage.

Therefore, there is a need to design an expandable polymeric valve to address the above problems.

SUMMARY OF THE INVENTION

In an embodiment of the present invention, provided is an expandable polymeric heart valve that is expandable after valve damage by optimizing the insert structure while ensuring blood flow properties in the original state of the valve for normal use. An expandable polymeric heart valve provided by an embodiment of the present invention includes valve leaflets and a valve frame. The valve frame has a hollow cylindrical structure. One end of the valve frame is provided with a plurality of column peaks at intervals in a circumferential direction and is correspondingly formed with column valleys. The valve further comprises an insert. The insert has a hollow cylindrical structure matching the valve frame. The insert is formed with positioning peaks and positioning valleys corresponding to the column peaks and the column valleys. The insert is adapted to be axially embedded in the valve frame. The insert is circumferentially provided with at least one expansion groove. The expansion groove has a closed state and an open state. The insert is provided with a limiting structure at outer walls of the two ends of the expansion groove. The limiting structure defines an expansion width when the expansion groove is in the open state. When the expansion groove is in the closed state, the insert has a cross section of a closed ring shape and a first diameter, while the heart valve is in an original state of normal use, allowing the blood to flow in one way. When the expansion groove is in the open state, the insert has a cross-section of a ring shape with an opening and a second diameter greater than the first diameter, while the heart valve is in an expansion state, allowing valve-in-valve implantation.

Optionally, the limiting structure comprises limiting pins and a limiting piece. The limiting pins are fixed to an outer wall of the insert and are respectively located at two ends of the expansion groove. The limiting piece is provided with a limiting groove. The limiting pin is provided in the limiting groove and movable along the limiting groove under the action of an external force. When the limiting pins are respectively located at two ends of the limiting groove, the expansion groove is in the open state.

Optionally, the limiting piece has a varying radius of curvature along the circumferential direction such that the limiting groove has a varying radius of curvature along the circumferential direction.

Optionally, when the expansion groove is in the closed state, the limiting pins are located in the middle of the limiting groove, the insert has a first diameter, and the radius of curvature of the middle of the limiting groove is approximately half of the first diameter; when the expansion groove is in the open state, the limiting pins are located at the ends of the limiting groove, the insert has a second diameter, and the radius of curvature of the end of the limiting groove is close to half of the second diameter; the radius of curvature of the limiting groove increases gradually from half of the first diameter to half of the second diameter in the circumferential direction from the middle to the end.

Optionally, the expansion groove is arranged at the positioning valley and the limiting groove is curved in an arc shape along the axial direction away from the positioning peak.

Optionally, the outer wall of the insert is formed with grooves at both ends of the expansion groove, and the total length of the grooves at both ends of the expansion groove is greater than or equal to the length of the limiting piece.

Optionally, the outer wall of the insert is provided with mating holes that mate with the limiting pins, and an end of the limiting pin is arranged in the mating hole to be fixedly connected to the insert.

Optionally, the distance between the outer wall of the insert and the outer wall of the valve frame is less than the distance between the inner wall of the insert and the inner wall of the valve frame.

Optionally, the valve frame is provided with a valve ring and a sealing membrane; the sealing membrane is connected to the valve ring and the valve frame via a suture; and the valve ring and the valve frame are made of a polymer material.

Optionally, the valve leaflets are made of a polymer material.

Compared with the prior art, the technical solution of the embodiments of the present invention has beneficial effects.

For example, the insert is embedded in the valve frame, the insert is provided with an expansion groove having a closed state and an open state. When the expansion groove is in the closed state, the insert is in the original state of normal use and the valve frame limits the opening of the expansion groove. At this time, there is no unevenness on the inner wall of the insert, without affecting the flow performance of the blood. When the valve is damaged, the expansion groove is opened by external force, and the expansion groove opening width is defined by the limiting structure. The insert is in an expansion state, so as to allow valve-in-valve implantation.

For another example, the radius of curvature of the limiting groove of the limiting piece is correspondingly set to change with the increase of the radius of the insert, so as to reduce the pressure required for balloon expansion to open the expansion groove in the secondary replacement surgery, and improve the efficiency of valve-in-valve implantation surgery.

For another example, the insert may be positioned farther from the inner wall of the valve frame and closer to the outer wall of the valve frame to facilitate outward radial expansion of the valve.

DESCRIPTION OF THE REFERENCE NUMERALS

1, valve frame; 11, column peak; 12, column valley;
2, valve leaflet;
3, insert; 31, expansion groove; 32, positioning peak; 33, positioning valley; 34, groove; 35, mating holes;
4, valve ring;
5, limiting structure; 51, limiting pin; 52, limiting piece; 521, limiting groove;
100, original state contour line of insert; 101, expansion state contour line of insert;
102, motion trajectory of limiting pin; and
200, original state of insert; 201, expansion state of insert.

DETAILED DESCRIPTION OF THE INVENTION

In order to make the purpose, features, and beneficial effects of the present invention more obvious and understandable, the detailed embodiments of the present invention will be described in detail below in conjunction with the accompanying drawings. It can be understood that the specific embodiments described below are only used to explain the present invention, and not to limit the present invention. Also, the same or similar reference numerals may be used in the drawings to refer to the same or similar elements in different embodiments, and descriptions of the same or similar elements in different embodiments and descriptions of elements, features, effects, etc. of the prior art may be omitted. It should be noted that the axial, radial, and circumferential directions described for the embodiments of the present invention refer to the axial, radial, and circumferential directions of the valve frame 1, respectively.

Referring to FIGS. 1-11, an embodiment of the present invention provides an expandable polymeric heart valve.

Figure 1:
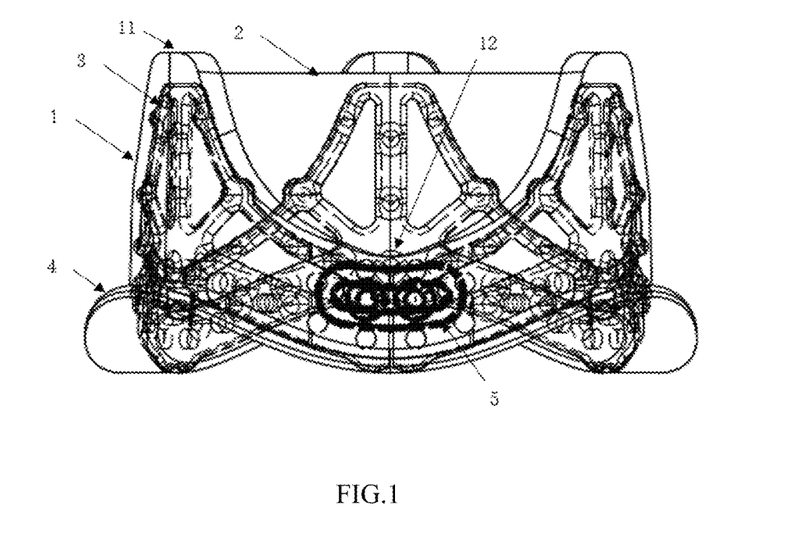
FIG. 1 is a structural schematic diagram of an expandable polymeric heart valve in an embodiment of the present invention.
Figure 2:
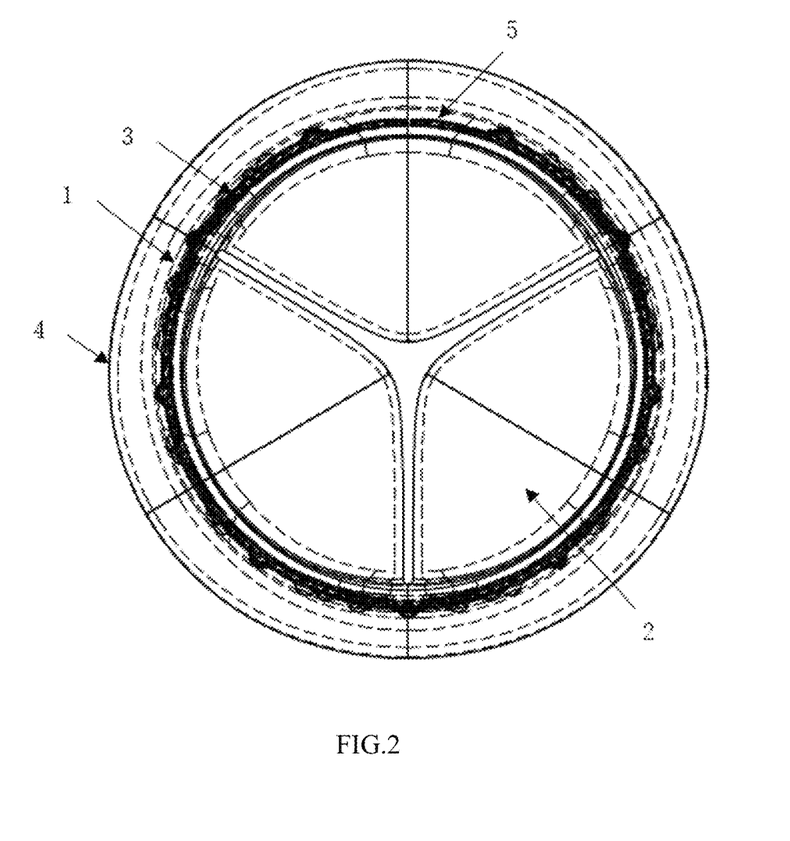
FIG. 2 is a top view of an expandable polymeric heart valve in an embodiment of the present invention.
Figure 3:
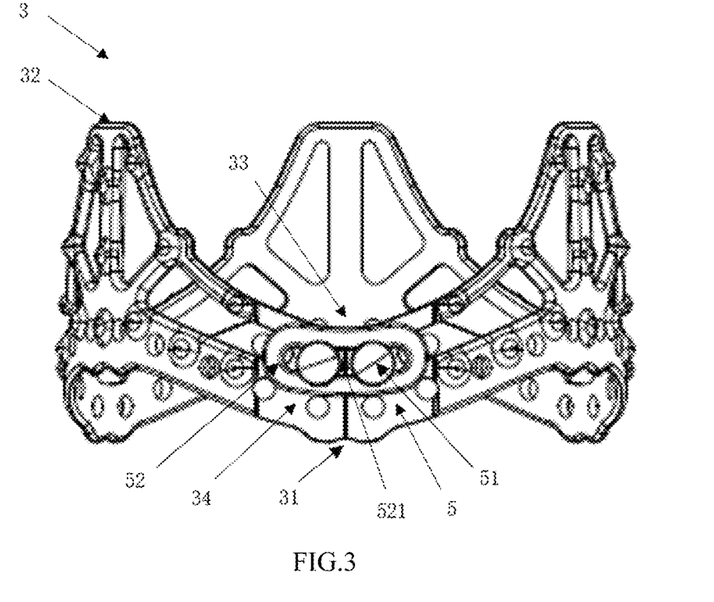
FIG. 3 is a structural schematic diagram of an insert in an original state in an embodiment of the present invention.
Figure 4:
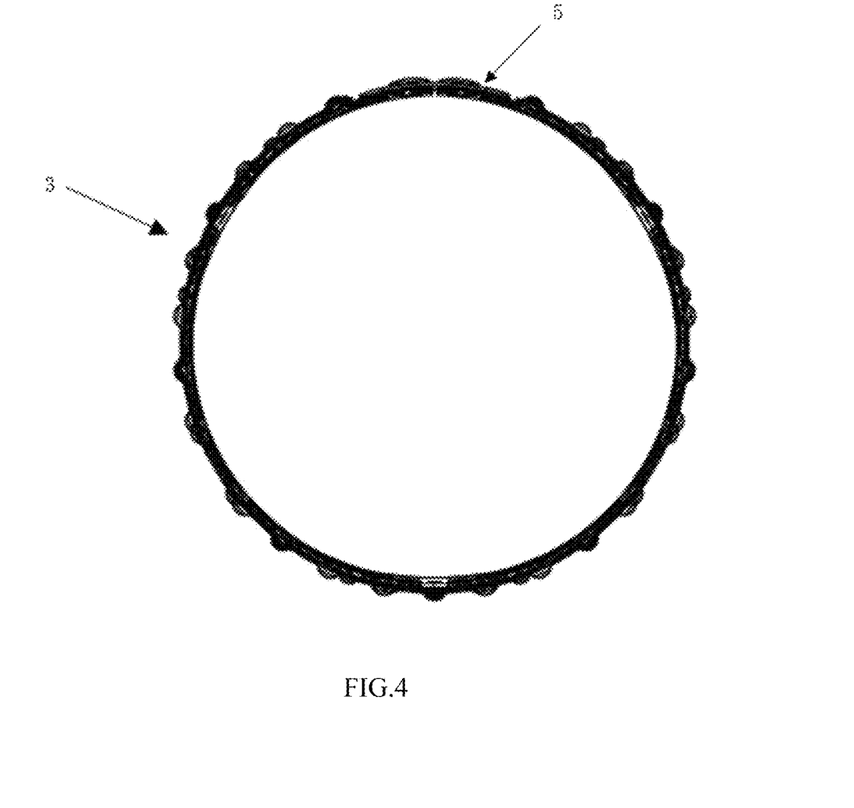
FIG. 4 is a top view of an insert in an original state in an embodiment of the present invention.
Figure 5:
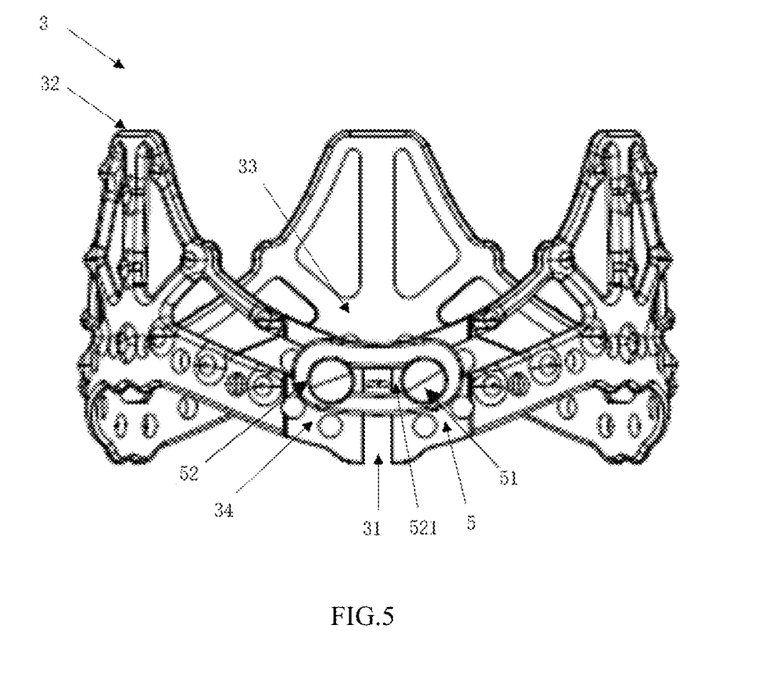
FIG. 5 is a structural schematic diagram of an insert in an expansion state in an embodiment of the present invention.

In a specific implementation, the expandable polymeric heart valve comprises valve leaflets 2 and a valve frame 1. The valve frame 1 has a hollow cylindrical structure. One end of the valve frame 1 is provided with a plurality of column peaks 11 at intervals in a circumferential direction and is correspondingly formed with column valleys 12. The valve further comprises an insert 3. The insert 3 has a hollow cylindrical structure matching the valve frame 1. The insert 3 is formed with positioning peaks 32 and positioning valleys 33 corresponding to the column peaks 11 and the column valleys 12. The insert 3 is adapted to be axially embedded in the valve frame 1. The insert 2 is circumferentially provided with at least one expansion groove 31. The expansion groove 31 has a closed state and an open state. The insert 3 is provided with a limiting structure 5 at an outer wall of the two ends of the expansion groove 31. The limiting structure 5 defines the expansion width of the expansion groove 31 in the open state. On the same expandable polymeric heart valve, along the circumferential direction of the insert 2, one set of expansion groove 31 and limiting structure 5 corresponding thereto may be provided (as shown in FIGS. 3 and 5), or two sets, three sets or more may be provided. When the expansion groove 31 is in the closed state, the insert 3 has a cross section of a closed ring shape and a first diameter, while the heart valve is in an original state of normal use, allowing the blood to flow in one way. At this time, there is no unevenness on the inner wall of the insert 3, so that there is no unevenness on the inner wall of the valve frame 1, without affecting the flow performance of the blood. When the expansion groove 31 is in the open state, the insert 3 has a second diameter greater than the first diameter and a cross-section of a ring shape with an opening, while the heart valve is in an expansion state, allowing valve-in-valve implantation.

When the valve is in the original state of normal use, the expansion groove 31 is in the closed state. The insert 3 is wrapped in the valve frame 1 to limit the opening of the expansion groove 31. There is no unevenness on the inner wall of the insert 3, and the inner wall of the valve is smooth, without affecting the flow performance of the blood. The insert 3 provides the radial supporting force. The structure is stable and the shape of the valve does not change. It will not deform during and after implantation, which would affect the use effect. When the valve is damaged and a valve-in-valve is required to be implanted, the expansion groove 31 can be opened by balloon expansion to expand the valve to the expansion state, allowing valve-in-valve implantation.

Referring to FIG. 5, in some embodiments, the limiting structure 5 comprises limiting pins 51 and a limiting piece 52. The limiting pins 51 are fixed to an outer wall of the insert 3 and are respectively located at two ends of the expansion groove 31. The limiting piece 52 has a limiting groove 521. The limiting pin 51 is provided in the limiting groove 521 and movable along the limiting groove 521 under the action of an external force. When the limiting pins 51 are respectively located at two ends of the limiting groove 521, the expansion groove 31 is in the open state.

In some embodiments, the limiting piece 52 has a varying radius of curvature along the circumferential direction such that the limiting groove 521 has a varying radius of curvature along the circumferential direction.

In some embodiments, when the expansion groove 31 is in the closed state, the limiting pins 51 are located in the middle of the limiting groove 521, the insert 3 has a first diameter, and the radius of curvature of the middle of the limiting groove 521 is approximately half of the first diameter. When the expansion groove 31 is in an open state, the limiting pins 51 are located at the ends of the limiting groove 521, the insert 3 has a second diameter, and the radius of curvature of the end of the limiting groove 521 is close to half of the second diameter. The radius of curvature of the limiting groove 521 increases gradually from half of the first diameter to half of the second diameter in the circumferential direction from the middle to the end.

Figure 6:
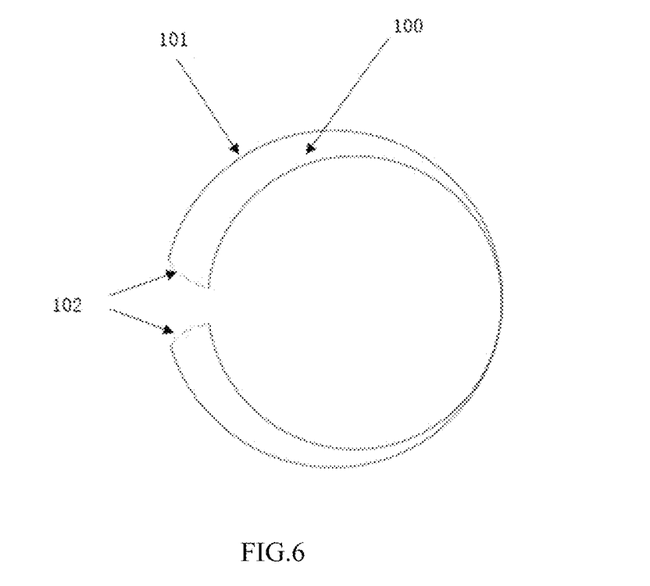
FIG. 6 is a top view trajectory schematic diagram of an insert in original and expansion states in an embodiment of the present invention.

In a specific implementation, when the expansion groove 31 of the insert 3 is expanded by the balloon, the circumferential movement track of the insert 3 and the limiting pins 51 is as shown in FIG. 6. The insert 3 expands from the original state contour line 100 of the insert to the expansion state contour line 101 of the insert, and at the same time, the limiting pins 51 move according to the motion trajectory 102 of limiting pins. During the expansion process, the motion trajectory of the limiting pins 51 has both circumferential motion and radial motion, so the overall motion trajectory is a curve. In the process of opening the expansion groove 31, the circumferential curve change of the limiting groove 521 of the limiting piece 52 coincides with the circumferential motion trajectory of the limiting pins 51, reducing the resistance when the limiting pins 51 move, reducing the pressure required for balloon expansion to open the expansion groove 31 in the secondary replacement surgery, and improving the efficiency of valve-in-valve implantation surgery.

Figure 7:
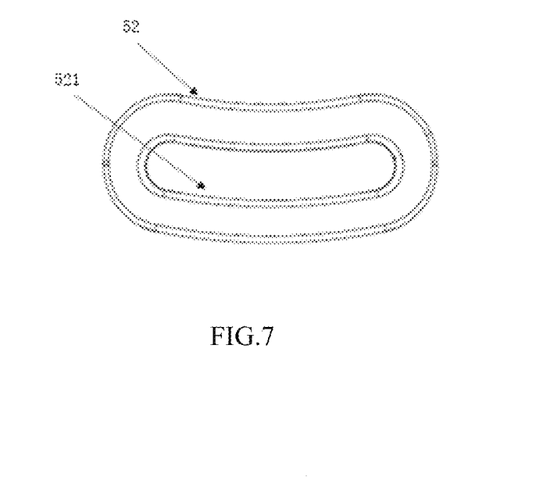
FIG. 7 is a structural schematic diagram of a limiting piece in an embodiment of the present invention.

Referring to FIG. 7, in some embodiments, the limiting groove 521 is curved in an arc shape along the axial direction away from the positioning peak 32.

Figure 8:
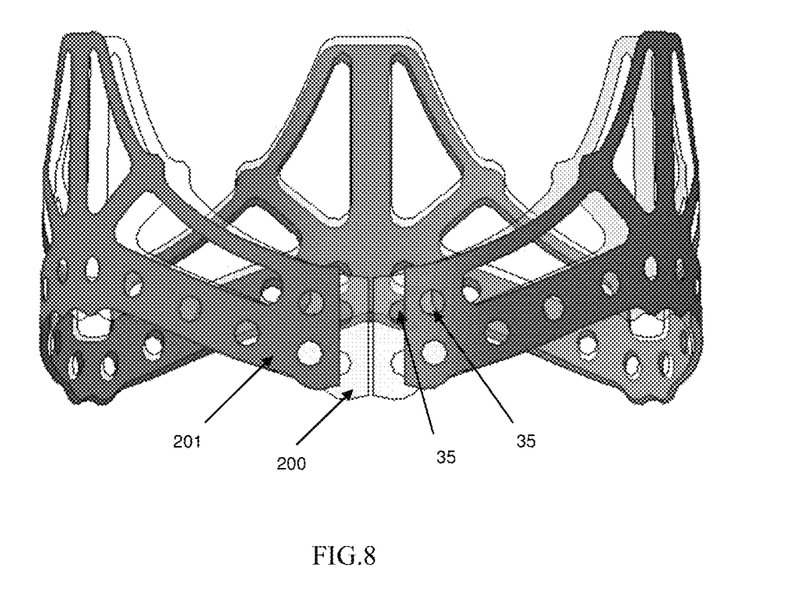
FIG. 8 is a side-view schematic diagram of an insert in original and expansion states in an embodiment of the present invention.
Figure 9:
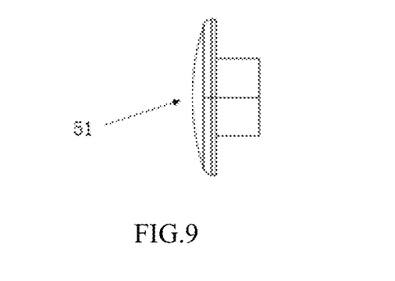
FIG. 9 is a limiting pin structure in an embodiment of the present invention.

In a specific implementation, the expansion groove 31 is provided at a positioning valley 33. When the expansion groove 31 of the insert 3 is expanded by the balloon, due to the force imbalance at various positions in the circumferential direction, the axial motion processes of the insert 3 and the limiting pins 51 are as shown in FIG. 8. The insert 3 expands from the original state 200 of the insert to the expansion state 201 of the insert, and at the same time, the limiting pin 51 moves with the mating hole 35. During the expansion process, the limiting pins 51 are displaced in the axial direction. The axial curve change of the limiting groove 521 of the limiting piece 52 coincides with the axial motion trajectory of the limiting pin 51, further reducing the resistance when the limiting pin 51 moves.

In some embodiments, three sets of expansion grooves 31 and limiting structures 5 corresponding thereto are provided. The three sets of expansion grooves 31 are respectively uniformly provided at the corresponding three positioning valleys 33. The limiting grooves 521 are straight in the axial direction. At this time, when the expansion grooves 31 of the insert 3 is expanded by the balloon, the force is balanced at various positions in the circumferential direction.

In some embodiments, three sets of expansion grooves 31 and limiting structures 5 corresponding thereto are provided. The three sets of expansion grooves 31 are non-uniformly provided on the insert 3. The limiting grooves 521 are curved in an arc shape in the axial direction away from the positioning peaks 32. At this time, when the expansion grooves 31 of the insert 3 are expanded by the balloon, the force is unbalanced at various positions in the circumferential direction. During the expansion process, the limiting pins 51 are displaced in the axial direction. The axial curve change of the limiting groove 521 of the limiting piece 52 coincides with the axial motion trajectory of the limiting pins 51, further reducing the resistance when the limiting pins 51 move.

In some embodiments, grooves 34 are formed at both ends of the outer wall of the insert 3 at the two ends of the expansion groove 31. The total length of the grooves 34 at the two ends of the expansion groove 31 is greater than or equal to the length of the limiting piece 52. The limiting pins 51 and the limiting piece 52 are mated in the region where the groove 34 is located. The thickness of the insert 3 in the region of the groove 34 is less than in other regions, reducing the force required for expansion of the valve and, at the same time reducing the overall thickness in the region of the limiting structure 5, reducing the bulging of the outer wall.

Figure 10:
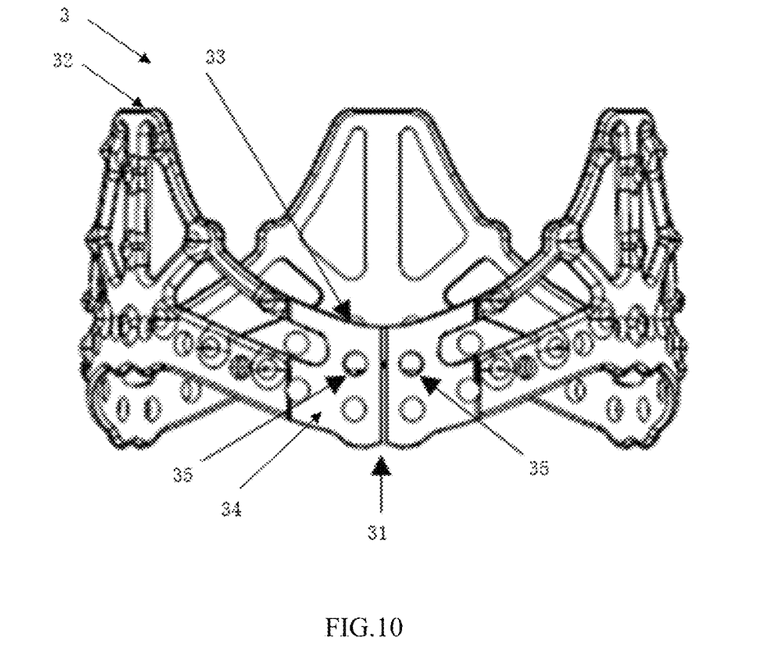
FIG. 10 is a schematic diagram of an insert with a limiting structure being removed in the embodiment of the present invention.

Referring to FIG. 10, in some embodiments, the outer wall of the insert 3 is provided with mating holes 35 that mate with limiting pins 51. The end of the limiting pin 51 is provided in the mating hole 35 and is fixedly connected to the insert 3. The limiting pin 51 can be connected to the mating hole 35 of the insert 31 by laser welding, gluing, interference fitting, etc.

Figure 11:
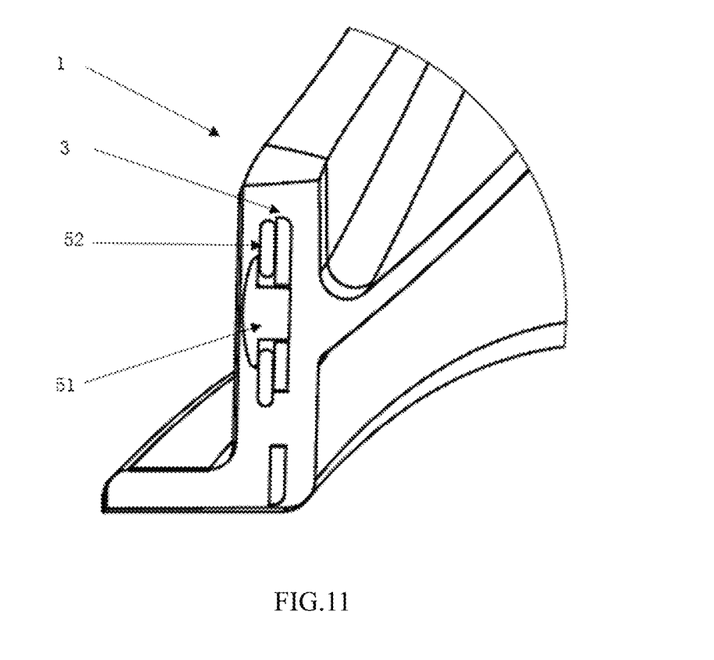
FIG. 11 is a cross-sectional view of an expandable polymeric heart valve according to an embodiment of the present invention.

Referring to FIG. 11, in some embodiments, the distance between the outer wall of the insert 3 and the outer wall of the valve frame 1 is less than the distance between the inner wall of the insert 3 and the inner wall of the valve frame 1. The insert 3 and the limiting structure 5 are positioned farther from the inner wall of the valve frame 1 and closer to the outer wall of the valve frame 1, which facilitates outward radial expansion of the valve.

In some embodiments, the valve frame 1 is provided with a valve ring 4 and a sealing membrane. The sealing membrane is connected to the valve ring 4 and the valve frame 1 via a suture. The valve ring 4 and the valve frame 1 are both made of polymer materials. The valve leaflets 2 is made of a polymer material. The polymer materials of the valve frame 1, valve leaflet 2, and valve ring 4 may be the same or different. The valve leaflet 2 can be attached to the valve frame 1 by dipping, spraying, molding, injection molding, sewing, etc. and the valve ring 4 can also be attached to the valve frame 1 by dipping, spraying, molding, injection molding, sewing, etc.

In a simulation experiment, the balloon-inflated valve is used to simulate the expansion process in actual use. Since the insert 3 is completely wrapped by the valve frame 1, the valve frame 1 restricts the opening of the expansion groove 31. In a free state, the inner diameter of the valve is 23.37 mm; under the low inflation pressure of balloon (<0.5 atm), the inner diameter of valve is 23.41 mm. In normal use, the valve size will not change basically, which will not affect the fatigue performance and treatment effect of valve. Since no pressure exceeding 0.5 atm exists in the human body, the stability of the overall structure of the valve is ensured. In the case of higher inflation pressure (2-6 atm), the expansion groove 31 is opened to the maximum, and the inner diameter of the valve is 25.90 mm, increasing the opening area so that the transcatheter valve-in-valve product with a larger size can be implanted, so as to obtain better treatment effect and improve the valve durability.

In view of the foregoing, according to embodiments of the present invention, an insert 3 is embedded in the valve frame 1. The insert 3 is provided with an expansion groove 31 having a closed state and an open state. When the expansion groove 31 is in a closed state, the insert 3 is in an original state of normal use and the valve frame 1 limits the opening of the expansion groove 31. At this time, there is no unevenness on the inner wall of the insert 3, without affecting the flow performance of the blood. When the valve is damaged, the expansion groove 31 is opened by the external force, and the opening width of the expansion groove 31 is defined by the limiting structure 5. The insert 3 is in an expansion state, so as to allow valve-in-valve implantation.

Further, according to embodiments of the present invention, the radius of curvature of the limiting groove 521 of the limiting piece 52 is correspondingly set to with the increase of the radius of the insert 3, so as to reduce the pressure required for balloon expansion to open the expansion groove 31 in the secondary replacement surgery, and improve the efficiency of valve-in-valve implantation surgery.

Further, the insert 3 of an embodiment of the present invention is positioned farther from the inner wall of the valve frame 1 and closer to the outer wall of the valve frame 1 to facilitate outward radial expansion of the valve.

While specific embodiments have been described above, these embodiments are not intended to limit the scope of the disclosure, even if a single embodiment is described with respect to only certain features. The examples of features provided in this disclosure are intended to be illustrative, and not limiting unless expressed differently. In a specific implementation, the technical features of one or more dependent claims can be combined with the technical features of independent claims as technically feasible according to actual needs, and the technical features from the corresponding independent claims can be combined in any appropriate way rather than just through specific combinations listed in the claims.

Although the present invention is disclosed above, the present invention is not limited thereto. Various changes and modifications may be made by one skilled in the art without departing from the spirit and scope of the present invention, which is intended to be limited only by the scope of the appended claims.

What is claimed is:

1. An expandable polymeric heart valve comprising valve leaflets and a valve frame, wherein the valve frame has a hollow cylindrical structure; one end of the valve frame is provided with a plurality of column peaks at intervals in a circumferential direction and is correspondingly formed with column valleys; the valve further comprises an insert; the insert has a hollow cylindrical structure matching the valve frame; the insert is formed with positioning peaks and positioning valleys corresponding to the column peaks and the column valleys; the insert is adapted to be axially embedded in the valve frame; the insert is circumferentially provided with at least one expansion groove; the expansion groove has a closed state and an open state; the insert is provided with a limiting structure at an outer wall of the two ends of the expansion groove; the limiting structure defines an expansion width when the expansion groove is in the open state; when the expansion groove is in the closed state, the insert has a cross section of a closed ring shape and a first diameter, without unevenness on an inner wall of the insert, so that there is no unevenness on an inner wall of the valve frame, while the heart valve is in an original state of normal use, allowing the blood to flow in one way, without affecting the flow performance of the blood; when the expansion groove is in the open state, the insert has a cross-section of a ring shape with an opening and a second diameter greater than the first diameter, while the heart valve is in an expansion state, allowing valve-in-valve implantation; the limiting structure comprises limiting pins and a limiting piece; the limiting pins are fixed to an outer wall of the insert and are respectively located at two ends of the expansion groove; the limiting piece is provided with a limiting groove; the limiting pin is provided in the limiting groove and movable along the limiting groove under the action of an external force; when the limiting pins are respectively located at two ends of the limiting groove, the expansion groove is in the open state; the outer wall of the insert is formed with grooves at both ends of the expansion groove; the total length of the grooves at both ends of the expansion groove is greater than or equal to the length of the limiting piece.

2. The expandable polymeric heart valve according to claim 1, wherein the limiting piece has a varying radius of curvature along the circumferential direction such that the limiting groove has a varying radius of curvature along the circumferential direction.

3. The expandable polymeric heart valve according to claim 2, wherein when the expansion groove is in the closed state, the limiting pins are located in the middle of the limiting groove, the insert has a first diameter, and the radius of curvature of the middle of the limiting groove is approximately half of the first diameter; when the expansion groove is in the open state, the limiting pins are located at the ends of the limiting groove, the insert has a second diameter, and the radius of curvature of the end of the limiting groove is close to half of the second diameter; the radius of curvature of the limiting groove increases gradually from half of the first diameter to half of the second diameter in the circumferential direction from the middle to the end.

4. The expandable polymeric heart valve according to claim 1, wherein the expansion groove is arranged at the positioning valley and the limiting groove is curved in an arc shape along the axial direction away from the positioning peak.

5. The expandable polymeric heart valve according to claim 1, wherein the outer wall of the insert is provided with mating holes that mate with the limiting pins, and an end of the limiting pin is arranged in the mating hole to be fixedly connected to the insert.

6. The expandable polymeric heart valve according to claim 1, wherein a distance between the outer wall of the insert and an outer wall of the valve frame is less than a distance between the inner wall of the insert and the inner wall of the valve frame.

7. The expandable polymeric heart valve according to claim 1, wherein the valve frame is provided with a valve ring and a sealing membrane; the sealing membrane is connected to the valve ring and the valve frame via a suture; and the valve ring and the valve frame are made of a polymer material.

8. The expandable polymeric heart valve according to claim 1, wherein the valve leaflets are made of a polymer material.

\* \* \* \* \*